United States Patent [19]

Winchel

[11] Patent Number: Plant 6,100

[45] Date of Patent: Feb. 9, 1988

[54] HYBRID TEA ROSE PLANT 'DOROTHY ANNE'

[75] Inventor: Joseph F. Winchel, Harbor City, Calif.

[73] Assignee: John C. Walter, Grand Saline, Tex.

[21] Appl. No.: 816,863

[22] Filed: Jan. 7, 1986

[51] Int. Cl.[4] ..... A01H 5/00

[52] U.S. Cl. ..... Plt./11

[58] Field of Search ..... Plt./11-18

*Primary Examiner*—James R. Feyrer

[57] ABSTRACT

A new and distinct variety of hybrid tea rose produced by me by crossing First Prize (U.S. Plant Pat. No. 2,774) with Lady X (U.S. Plant Pat. No. 2,691).

1 Drawing Figure

The present invention relates to a new and distinct variety of rose plant of the hybrid tea class which was originated by crossing First Prize (U.S. Plant Pat. No. 2,774) with Lady X (U.S. Plant Pat. No. 2,691). The new and distinct variety was asexually reproduced by budding in Shreveport, La. 71105, the seedling was taken to Harbor City, Calif. 90710 where it was asexually reproduced by budding and observed.

This rose differs from its seed parent First Prize by having a very sturdy bush that produces more basal breaks and more abundant foliage, with blooms that usually come one to a stem, have a shorter bud, more petals, and are a different color.

This rose differs from its pollen parent Lady X by having a very sturdy bush with more abundant foliage and more thorns, with blooms that have more and thicker petals to give better form and substance, and are a different color.

The accompanying drawing shows typical specimens of the growth and habit of my new variety in different stages of development in October 1985 in Harbor City, Calif., the color as nearly true as it is possible to make the same in a color illustration of this character. The colors in the following description are taken from the color chart of The Royal Horticultural Society, where a color designation number is shown. The other color designations are ordinary dictionary terms, where no color number is assigned.

The following is a detailed description of my new rose variety:

Type: Upright bush, seedling, for garden decoration.
Class: Hybrid tea.
Commercial synonym: Dorothy Anne.

THE FLOWER

Locality where grown: Shreveport, La.; Harbor City, Calif.; Canton, Tex.
Flowers borne: Usually singly, occasionally a spray.
Continuity: Continuous throughout the growing season.
Fragrance: Very slight (sweet to fruity).
Bud:

*Size.*—Medium-large.
*Form.*—Ovoid.
*Color.*—A blend of reds (a brushing of 53A and B on 56C and D)with a base of yellow (2D).
*Sepals.*—Long, with two often longer than bud, some notched, some smooth.

*Peduncle.*—8-10 cm., with regular tiny prickles, strong, erect, usually reddish green in color.

Bloom:

*Size when fully opened.*—To 15 cm. average.
*Borne.*—Singly with an occasional spray.
*Form.*—High centered at first, then petals roll outward in a firm wrap, finally opening so each petal stands alone with upper edges rolled down.
*Petalage.*—30-40 petals, regularly arranged.
*Color.*—Outer petals: Pink blend with red (53C and D) lightly brushed on red (56D). Reverse of petals: Pink blend (red 53 B and D) brushed on light pink (red 56 C and D) with base of yellow (2 B and C). Inner petals: Blended cream (orange 159 B, C, and D). General tone from distance: Pink with cream center. Color change: The photosensitive pigments in the petals cause more pink "brushing" on more petals in the bright sunlight, so after three days almost all of the petals will be "brushed" with pink. Pink (red 53 C and D) brushed on light pink (red 56D) and cream (yellow-white 58D).

Petals:

*Texture.*—Thick.
*Appearance.*—Inside, velvety; outside, velvety.
*Form.*—Tulip shaped with slight notch in center.
*Arrangement.*—Regularly arranged.
*Petaloids in center.*—Few.
*Persistence.*—Drop off cleanly.
*Lasting quality.*—Holds well on plant and as cut flower.

REPRODUCTIVE ORGANS

Stamens, filaments, and anthers:

*Arrangement.*—Regularly arranged around styles.
*Color.*—Yellow.

Pollen: Yellow.
Styles: Uneven lengths.
Stigmas: Yellow.
Hips: Very few, globular, medium size, dark brown, seeds protrude.

PLANT

Growth: Upright, vigorous, compact, uneven branching: Height 120-150 cm.
Foliage: Compound, 5 to 7 leaflets.
Size: Medium.
Quantity: Abundant.
Color:

(Continued on next page.)

*New foliage.*—Upper — green with red tinge; under — reddish green.

*Old foliage.*—Upper — dark green; under — softer green.

Shape: Oval, pointed.

Texture: Upper — semi-glossy; under — matte.

Edge: Tiny serrations, slightly reddish in color.

Leaf stem: Color: green; Underside: lighter green.

Stipules: Large, slightly bearded.

Resistance to disease: Blackspot: good; Mildew: good; Rust: never experienced it.

Wood:

*New wood.*—Color: reddish green, Bark: smooth.

*Old wood.*—Color: green. Bark: smooth.

Thorns:

*Quantity.*—On main stalk — many of all sizes. On laterals — many.

*Length.*—Large and small, very pointed, curved downward.

*Color.*—Red when young, Brownish tan when older and bark is still green.

*Position.*—Irregular, very frequently.

Prickles:

*Quantity.*—Profuse on main stalk, laterals, and peduncle.

Winter hardiness: Winter hardy if protected.

I claim:

1. A new and distinct variety of rose plant of the hybrid tea class, substantially as herein shown and described, characterized by the combination of a sturdy, upright plant with abundant foliage and many thorns, carrying usually one bloom per stem that is large, high-centered, with a striking color of pink with cream center, with sun exposure producing more attractive pink coloration on the petals, and of good keeping qualities both on the bush and as a cut flower.

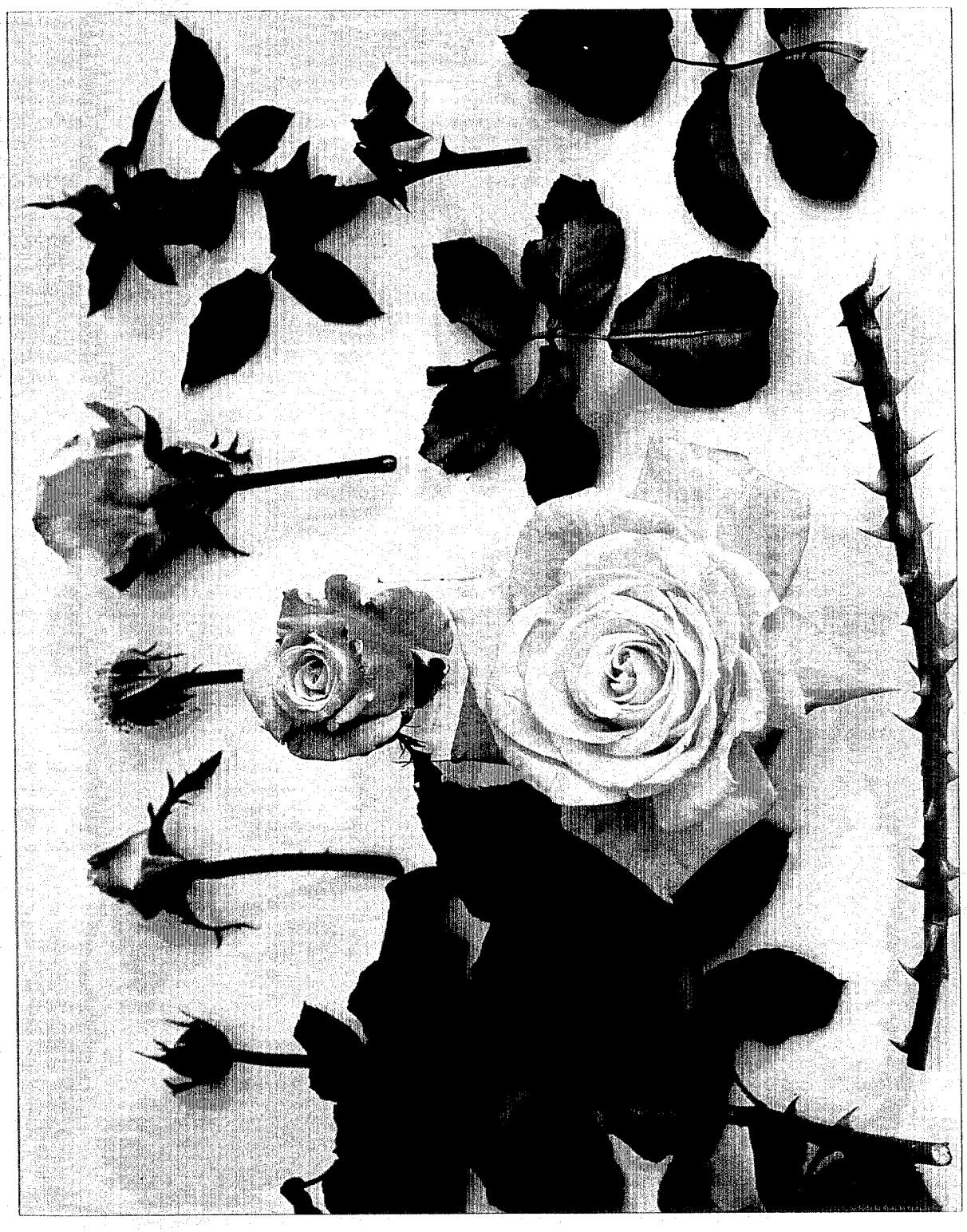

* * * * *